United States Patent
Zan et al.

(10) Patent No.: US 9,748,482 B2
(45) Date of Patent: Aug. 29, 2017

(54) SEMICONDUCTOR SENSING DEVICE COMPRISING CONDUCTIVE NANOWIRES AND MANUFACTURING METHOD THEREOF

(71) Applicant: E Ink Holdings Inc., Hsinchu (TW)

(72) Inventors: Hsiao-Wen Zan, Hsinchu (TW);
Chuang-Chuang Tsai, Hsinchu (TW);
Pei-Chen Yu, Hsinchu (TW);
Ming-Yen Chuang, Hsinchu (TW);
Chia-Chun Yeh, Hsinchu (TW)

(73) Assignee: E Ink Holdings Inc., Hsinchu (TW)

( * ) Notice: Subject to any disclaimer, the term of this patent is extended or adjusted under 35 U.S.C. 154(b) by 0 days.

(21) Appl. No.: 14/564,106

(22) Filed: Dec. 9, 2014

(65) Prior Publication Data

US 2015/0233851 A1    Aug. 20, 2015

Related U.S. Application Data

(60) Provisional application No. 61/940,851, filed on Feb. 18, 2014.

(30) Foreign Application Priority Data

Oct. 13, 2014    (TW) .............................. 103135379 A

(51) Int. Cl.
*H01L 51/00* (2006.01)
*G01N 27/12* (2006.01)
*G01N 27/414* (2006.01)

(52) U.S. Cl.
CPC ....... *H01L 51/0001* (2013.01); *G01N 27/125* (2013.01); *G01N 27/4141* (2013.01); *G01N 27/4146* (2013.01)

(58) Field of Classification Search
CPC ........... H01L 29/0676; H01L 21/02603; H01L 29/0669; G01N 27/4146; G01N 27/4141; G01N 27/4143
See application file for complete search history.

(56) References Cited

U.S. PATENT DOCUMENTS 7,646,074 B2    1/2010    Shim
8,240,190 B2    8/2012    Chen et al.
(Continued)

FOREIGN PATENT DOCUMENTS

CN    1795371    6/2006
CN    1847838    10/2006
(Continued)

OTHER PUBLICATIONS

"Office Action of Taiwan Counterpart Application", dated May 25, 2016, p. 1-7.
(Continued)

*Primary Examiner* — Davienne Monbleau
*Assistant Examiner* — Leslie Pilar Cruz
(74) *Attorney, Agent, or Firm* — Jianq Chyun IP Office

(57) ABSTRACT

A semiconductor sensing device that includes a nanowire conductive layer, a semiconductor sensing layer, and a conductive layer is provided. The nanowire conductive layer includes a plurality of connected conductive nanowires, and gaps are formed between the conductive nanowires. The semiconductor sensing layer is electrically connected to the nanowire conductive layer. The conductive layer is electrically connected to the semiconductor sensing layer. The semiconductor sensing layer is located between the nanowire conductive layer and the conductive layer. A manufacturing method of a semiconductor sensing device is also provided.

6 Claims, 6 Drawing Sheets

(56) References Cited

U.S. PATENT DOCUMENTS

| | | |
|---|---|---|
| 8,338,897 B2 | 12/2012 | Kim et al. |
| 8,593,714 B2 | 11/2013 | Agrawal et al. |
| 8,603,836 B2 | 12/2013 | Yoon et al. |
| 2004/0074785 A1 | 4/2004 | Holker et al. |
| 2010/0147684 A1 | 6/2010 | Park et al. |
| 2011/0097241 A1 | 4/2011 | Wang et al. |
| 2011/0197657 A1* | 8/2011 | Gole .................... G01N 27/127 73/31.05 |
| 2011/0227061 A1* | 9/2011 | Lee ........................ B82Y 30/00 257/43 |
| 2012/0097917 A1 | 4/2012 | Zhou et al. |
| 2013/0342221 A1 | 12/2013 | Virkar et al. |
| 2014/0291569 A1* | 10/2014 | Jeon ......................... C01G 9/02 252/62.9 R |

FOREIGN PATENT DOCUMENTS

| | | |
|---|---|---|
| CN | 1967231 | 5/2007 |
| CN | 101501481 | 8/2009 |
| CN | 101506648 | 8/2009 |
| TW | 201309586 | 3/2013 |
| WO | 2010022321 | 2/2010 |

OTHER PUBLICATIONS

Ming-Yen Chuang et al., "Gas permeable silver nanowire electrode for realizing vertical type sensitive gas sensor" Organic Electronics, vol. 15, Issue 11, Nov. 2014, pp. 2769-2774.

"Office Action of China Counterpart Application", dated Mar. 3, 2017, p. 1-p. 9.

* cited by examiner

SEMICONDUCTOR SENSING DEVICE COMPRISING CONDUCTIVE NANOWIRES AND MANUFACTURING METHOD THEREOF

CROSS-REFERENCE TO RELATED APPLICATION

This application claims the priority benefits of U.S. provisional application Ser. No. 61/940,851, filed on Feb. 18, 2014 and Taiwan application serial no. 103135379, filed on Oct. 13, 2014. The entirety of each of the above-mentioned patent applications is hereby incorporated by reference herein and made a part of this specification.

BACKGROUND OF THE INVENTION

Field of the Invention

The invention generally relates to a semiconductor device and a manufacturing method thereof. More particularly, the invention relates to a semiconductor sensing device and a manufacturing method thereof.

Description of Related Art

With the development of science and technology, semiconductors have been extensively applied to our daily lives. Among various types of applications of the semiconductors, gas sensing devices having the semiconductors have drawn more and more attention because the semiconductors are greatly sensitive to the gas which the semiconductors are in contact with. Specifically, after a gas sensing semiconductor is in contact with a specific gas, the electrical properties (e.g., the resistance) of the gas sensing semiconductor may correspondingly alter; therefore, through detecting and measuring the electrical properties of the gas sensing semiconductor, a user is able to determine whether said specific gas exists in the surroundings where the semiconductor is located.

When the semiconductor is applied to sense the gas, the measure of contact area between the semiconductor and the gas is a factor that directly contributes to the sensing sensitivity of the semiconductor; hence, an electrode covering the semiconductor lessens the sensing sensitivity of the semiconductor. In addition, the electrode electrically connected to the semiconductor may be designed to have the special structure according to the related art; alternatively, the electrode and the semiconductor may be composed of a plurality of microstructures, such that the contact area between the semiconductor and the gas can be expanded. However, gaps among the microstructures of the semiconductor are often filled with the microstructures (or the sub-structures) of the electrode while the microstructures (or the sub-structures) are formed, and thus the resultant structure is not satisfactory.

SUMMARY OF THE INVENTION

The invention is directed to a semiconductor sensing device that is characterized by exceptional sensing sensitivity.

The invention is further directed to a manufacturing method of a semiconductor sensing device; by applying the method, a highly sensitive semiconductor sensing device equipped with nanowire structures may be formed.

In an embodiment of the invention, a semiconductor sensing device that includes a nanowire conductive layer, a semiconductor sensing layer, and a conductive layer is provided. The nanowire conductive layer includes a plurality of connected conductive nanowires, and gaps are formed between the conductive nanowires. The semiconductor sensing layer is electrically connected to the nanowire conductive layer. The conductive layer is electrically connected to the semiconductor sensing layer. The semiconductor sensing layer is located between the nanowire conductive layer and the conductive layer.

In an embodiment of the invention, a manufacturing method of a semiconductor sensing device includes forming a conductive layer on a substrate, forming a semiconductor sensing layer, and forming a nanowire conductive layer on the semiconductor sensing layer by drop casting. The semiconductor sensing layer at least covers a portion of the conductive layer. The nanowire conductive layer includes a plurality of connected conductive nanowires, and gaps are formed between the conductive nanowires.

According to an embodiment of the invention, a material of the semiconductor sensing layer includes an organic semiconductor material.

According to an embodiment of the invention, a material of the semiconductor sensing layer includes an inorganic semiconductor material.

According to an embodiment of the invention, the semiconductor sensing device further includes a substrate, and the conductive layer is located between the semiconductor sensing layer and the substrate.

According to an embodiment of the invention, the semiconductor sensing device further includes a dielectric layer located between the semiconductor sensing layer and the conductive layer and between the semiconductor sensing layer and the substrate, wherein the conductive layer covers one portion of the substrate, the dielectric layer covers one portion of the conductive layer and another portion of the substrate, the semiconductor sensing layer covers the dielectric layer and a portion of the conductive layer exposed by the dielectric layer, and the nanowire conductive layer is located on the semiconductor sensing layer.

According to an embodiment of the invention, the conductive nanowires are connected in a random manner, so as to form the nanowire conductive layer.

According to an embodiment of the invention, a material of the semiconductor sensing layer includes indium-gallium-zinc oxide (IGZO), tin dioxide ($SnO_2$), zinc oxide (ZnO), iron oxide (e.g. $Fe_2O_3$), or a combination thereof.

According to an embodiment of the invention, the semiconductor sensing layer includes a plurality of semiconductor sensing pillars extending along a direction from the conductive layer to the nanowire conductive layer.

In view of the above, the semiconductor sensing device provided in an embedment of the invention has the nanowire conductive layer that allows the contact area between the semiconductor sensing layer and the gas to be expanded, thus enhancing the sensing sensitivity. The conductive nanowires of the nanowire conductive layer can also be prevented from being inserted into the gaps in the semiconductor sensing layer. In another aspect, according to the manufacturing method of the semiconductor sensing device provided herein, the nanowire conductive layer can be formed on the semiconductor sensing layer by drop casting, so as to form the highly sensitive semiconductor sensing device.

Several exemplary embodiments accompanied with figures are described in detail below to further describe the invention in details.

DETAILED DESCRIPTION OF DISCLOSED EMBODIMENTS

Figure 1A:
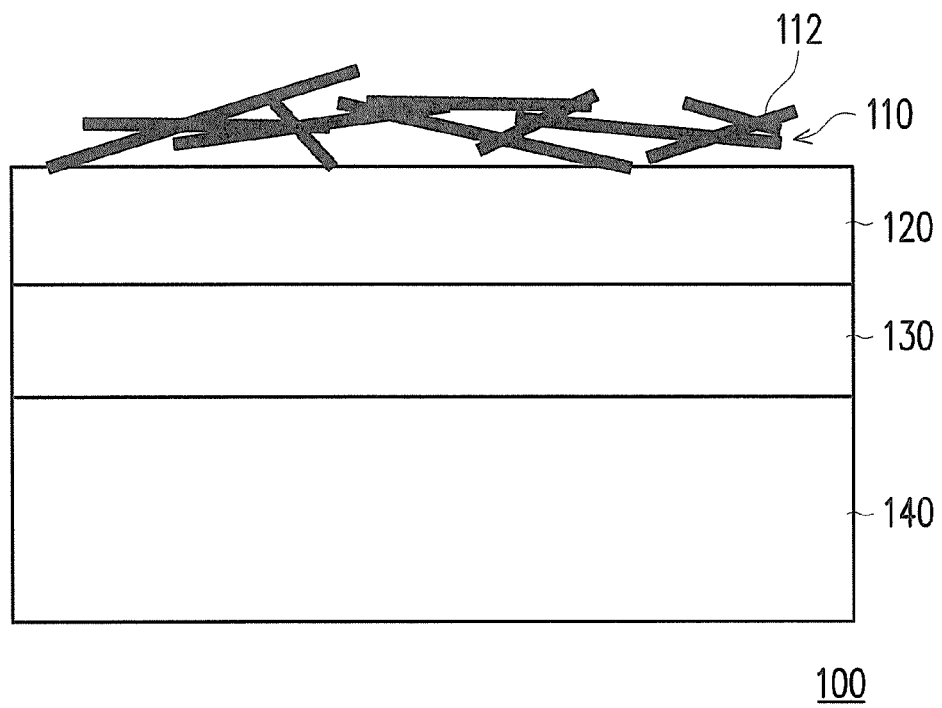
FIG. 1A is a cross-sectional diagram illustrating a semiconductor sensing device according to a first embodiment of the invention.

FIG. 1A is a cross-sectional diagram illustrating a semiconductor sensing device according to a first embodiment of the invention. With reference to FIG. 1A, in the present embodiment of the invention, a semiconductor sensing device 100 includes a nanowire conductive layer 110, a semiconductor sensing layer 120, and a conductive layer 130. The nanowire conductive layer 110 includes a plurality of connected conductive nanowires 112, and gaps are formed between the conductive nanowires 112. The semiconductor sensing layer 120 is electrically connected to the nanowire conductive layer 110. The conductive layer 130 is electrically connected to the semiconductor sensing layer 120, and the semiconductor sensing layer 120 is located between the nanowire conductive layer 110 and the conductive layer 130. In the semiconductor sensing device 100 provided herein, the gaps between the conductive nanowires 112 allow the semiconductor sensing layer 120 to be in contact with gases, so as to enhance the sensing sensitivity of the semiconductor sensing device 100.

As shown in FIG. 1A, in the first embodiment of the invention, the semiconductor sensing device 100 further includes a substrate 140, and the conductive layer 130 is located between the semiconductor sensing layer 120 and the substrate 140. According to the present embodiment, the conductive nanowires 112 are connected in a random manner, so as to form the nanowire conductive layer 110.

The semiconductor sensing layer 120 shown in FIG. 1A is made of an organic semiconductor material; however, the invention is not limited thereto. In another embodiment of the invention, the semiconductor sensing layer 120 may be made of an inorganic semiconductor material. Specifically, with reference to FIG. 1A, a material of the semiconductor sensing layer 120 provided in an embodiment of the invention includes indium-gallium-zinc oxide (IGZO) which may serve to sense moisture in air (i.e., humidity of air). According to another embodiment, a material of the semiconductor sensing layer 120 includes tin dioxide ($SnO_2$), zinc oxide (ZnO), or iron oxide (e.g. $Fe_2O_3$) which may serve to sense a fuel gas in air. According to yet another embodiment, a material of the semiconductor sensing layer 120 includes tin dioxide ($SnO_2$) which may serve to sense carbon monoxide (CO) in air. In other embodiments of the invention, the material of the semiconductor sensing layer 120 is not limited to said organic semiconductor material, said inorganic material, or said semiconductor oxide material and may be a combination of said materials and other materials according to the gases to be sensed.

Particularly, in an embodiment of the invention, the electrical properties of the semiconductor sensing layer 120 can be measured by electrically connecting the nanowire conductive layer 110 and the conductive layer 130 of the semiconductor sensing device 100. As described herein, once the semiconductor sensing layer 120 is in contact with a to-be-sensed gas, the electrical properties (e.g., resistance or conductivity) of the semiconductor sensing layer 120 may be changed, and such changes may be learned by measuring the electrical properties of the semiconductor sensing layer 120.

Figure 1B:
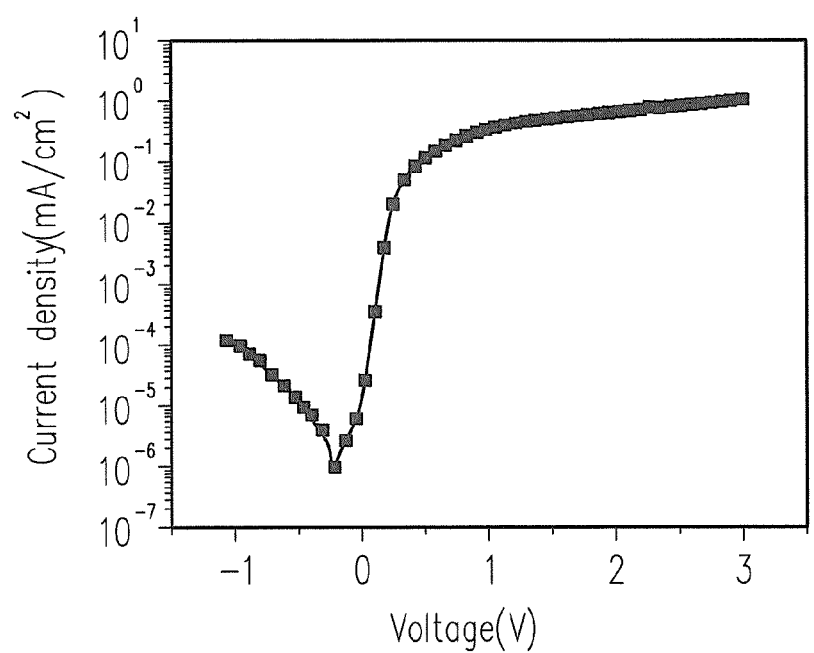
FIG. 1B is a schematic diagram illustrating a voltage to current density correlation of the semiconductor sensing device according to the first embodiment of the invention.

FIG. 1B is a schematic diagram illustrating a voltage to current density correlation of the semiconductor sensing device 100 according to the first embodiment of the invention. With reference to FIG. 1B, in the first embodiment of the invention, the conductive nanowires 112 are silver nanowires, for instance, and the material of the semiconductor sensing layer 120 includes poly(3-hexylthiophene) (P3HT). It can be learned from FIG. 1B that the nanowire conductive layer 110 provided in the present embodiment can effectively serve as the electrode of the semiconductor sensing device 100, such that the electrical properties of the semiconductor sensing layer 120 can be measured to learn the concentration of the to-be-sensed gas in contact with the semiconductor sensing layer 120.

Figure 2:
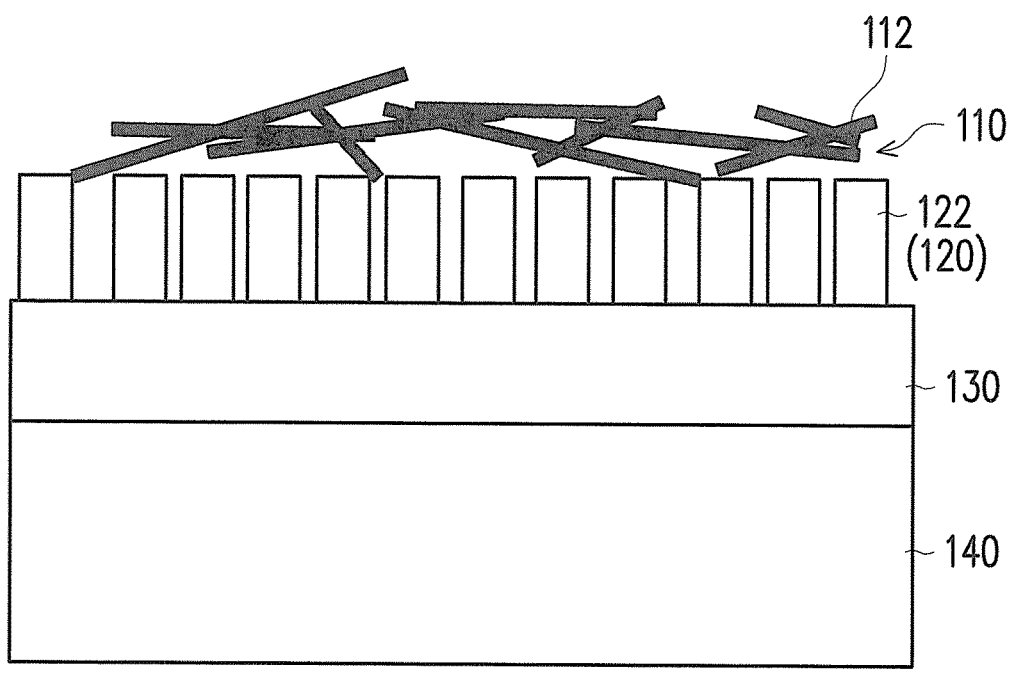
FIG. 2 is a cross-sectional diagram illustrating a semiconductor sensing device according to a second embodiment of the invention.

FIG. 2 is a cross-sectional diagram illustrating a semiconductor sensing device according to a second embodiment of the invention. With reference to FIG. 2, the semiconductor sensing device 200 provided in the second embodiment of the invention is similar to the semiconductor sensing device 100 described above, while the difference therebetween lies in that the semiconductor sensing layer 120 includes a plurality of semiconductor sensing pillars 122 extending along a direction from the conductive layer 130 to the nanowire conductive layer 110. Hence, in the present embodiment, the sensing sensitivity of the semiconductor sensing device 200 can be enhanced by the conductive nanowires 112; what is more, the semiconductor sensing layer 120 composed of the semiconductor sensing pillars 122 can be in contact with gases to a greater extent because the surface area of the semiconductor sensing layer 120 is expanded, and thus the sensing sensitivity can be further improved. Besides, in the present embodiment, the conductive nanowires 112 are connected in a random manner to form the nanowire conductive layer 110; at the same time, the connected conductive nanowires 112 can be prevented from falling into the gaps between the semiconductor sensing pillars 122, thus ensuring the favorable quality of the semiconductor sensing device 200.

Figure 3A:
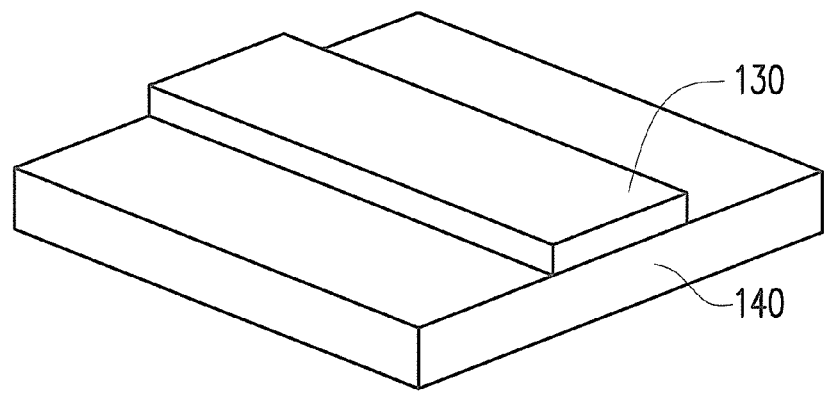
FIG. 3A to FIG. 3F are schematic diagrams illustrating steps of a manufacturing method of a semiconductor sensing device according to a third embodiment of the invention.
Figure 3B:
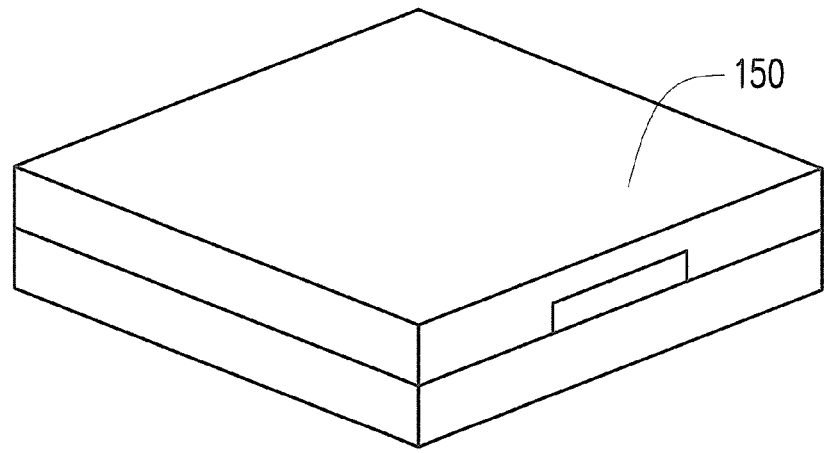
Figure 3C:
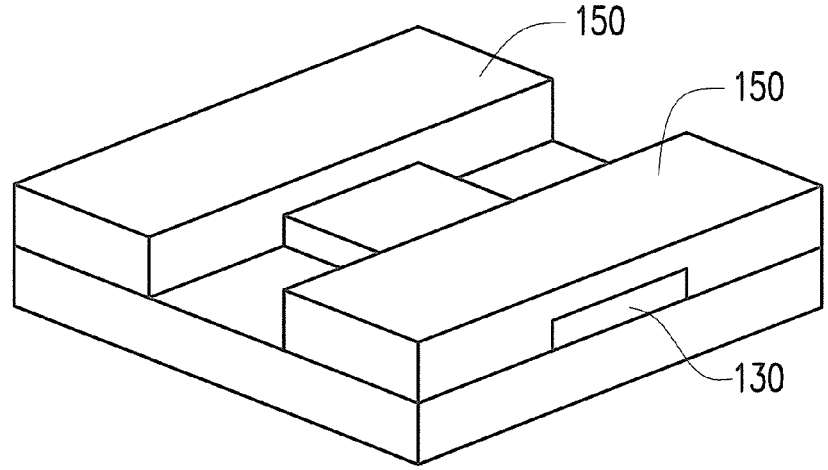
Figure 3D:
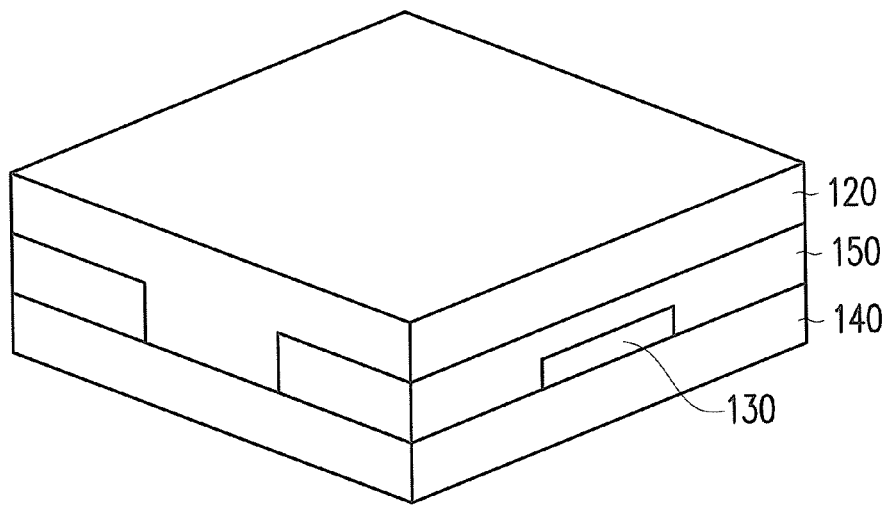
Figure 3E:
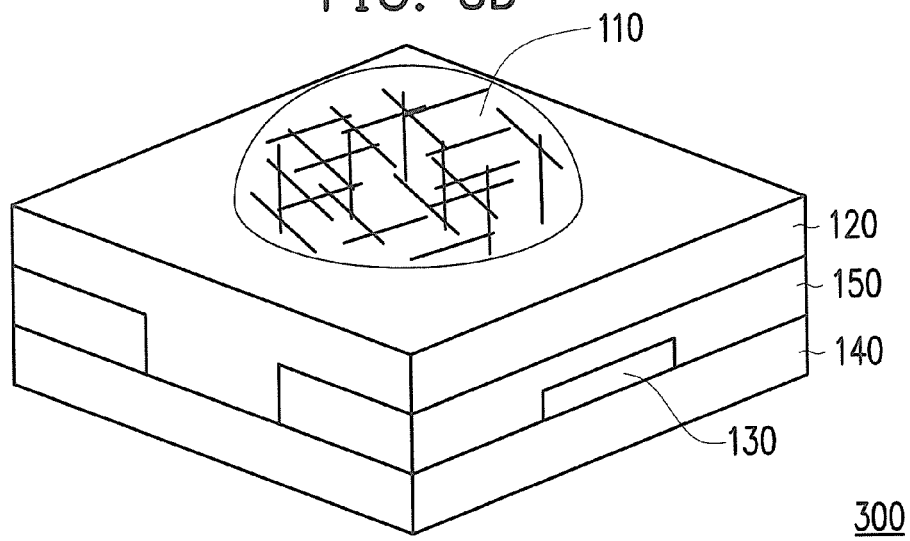
Figure 3F:
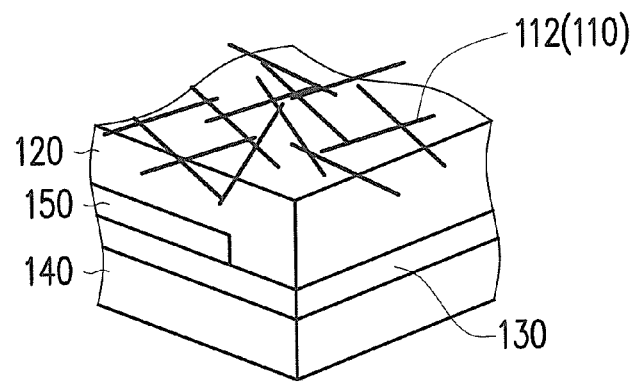

FIG. 3A to FIG. 3F are schematic diagrams illustrating steps of a manufacturing method of a semiconductor sensing device according to a third embodiment of the invention. Note that FIG. 3F is a partially enlarged cross-sectional diagram of FIG. 3E. With reference to FIG. 3A to FIG. 3F, in the third embodiment of the invention, a manufacturing method of a semiconductor sensing device 300 includes forming a conductive layer 130 on a substrate 140, forming a semiconductor sensing layer 120, and forming a nanowire conductive layer 110 on the semiconductor sensing layer 120 by drop casting. The semiconductor sensing layer 120 at least covers a portion of the conductive layer 130. Here, the nanowire conductive layer 110 includes a plurality of connected conductive nanowires 112, and gaps are formed between the conductive nanowires 112. Particularly, in the present embodiment, the nanowire conductive layer 110 is formed by dropping solutions (having the conductive nanowires 112) on the semiconductor sensing layer 120 and drying (e.g., by baking) the semiconductor sensing layer 120 on which the solutions are dropped, such that the conductive nanowires 112 form the nanowire conductive layer 110.

With reference to FIG. 3A to FIG. 3F, in the third embodiment of the invention, the semiconductor sensing device 300 further includes a dielectric layer 150 that is located between the semiconductor sensing layer 120 and the conductive layer 130 and between the semiconductor sensing layer 120 and the substrate 140. The conductive layer 130 covers one portion of the substrate 140, the dielectric layer 150 covers one portion of the conductive layer 130 and another portion of the substrate 140, the semiconductor sensing layer 120 covers the dielectric layer 150 and a portion of the conductive layer 130 exposed by the dielectric layer 150, and the nanowire conductive layer 110 is located on the semiconductor sensing layer 120.

That is, as shown in FIG. 3A to FIG. 3F, in the manufacturing method of the semiconductor sensing device 300 provided in the third embodiment of the invention, after the conductive layer 130 is formed on the substrate 140, the dielectric layer 150 is further formed on one portion of the conductive layer 130 and another portion of the substrate 140 exposed by the conductive layer 130, and the semiconductor sensing layer 120 further covers the dielectric layer 150.

Particularly, as shown in FIG. 3B and FIG. 3C, in the manufacturing method of the semiconductor sensing device 300 provided in the third embodiment of the invention, after the dielectric layer 150 is formed, a portion of the dielectric layer 150 is further etched to define an active area (e.g., the main area for sensing the gas). Here, the portion of the dielectric layer 150 is etched by plasma, for instance, which should however not be construed as a limitation to the invention. With reference to FIG. 3B and FIG. 3D, in the present embodiment, the dielectric layer 150 and the semiconductor sensing layer 120 are formed by spin coating, which should however not be construed as a limitation to the invention.

Figure 4:
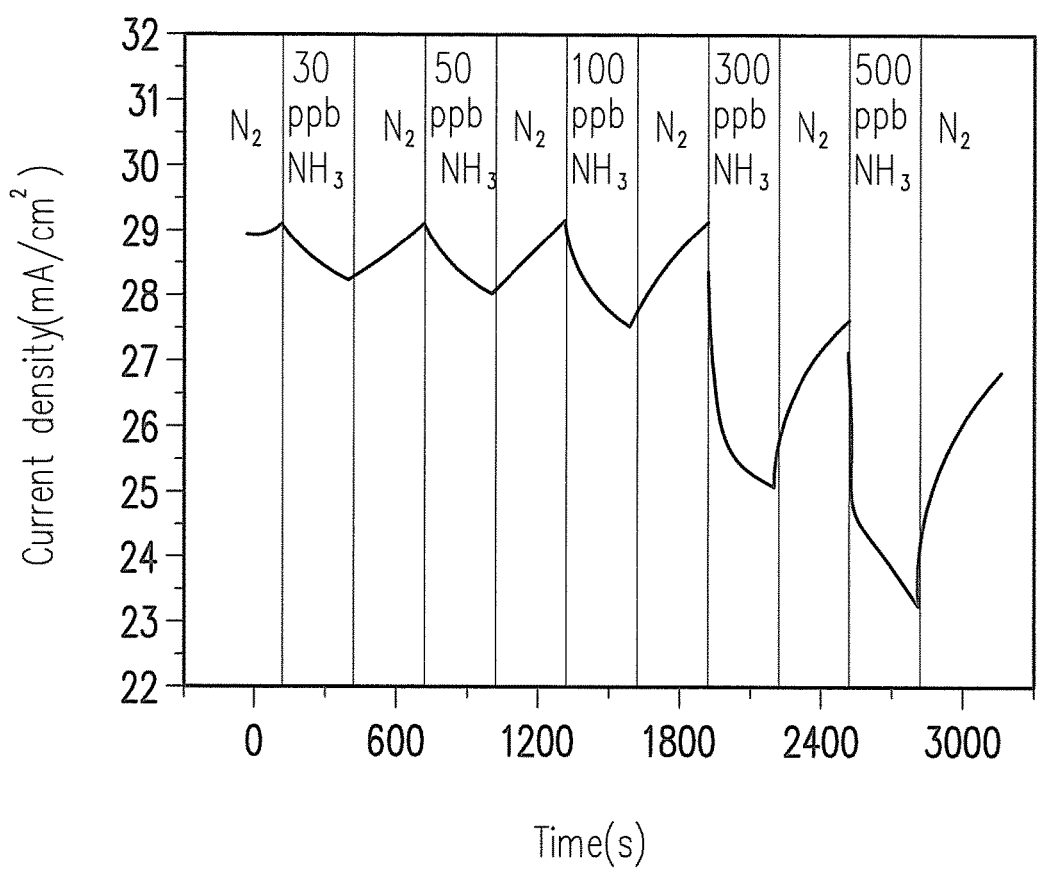
FIG. 4 is a schematic diagram illustrating variations in current density of gases to be sensed by the semiconductor sensing device according to the third embodiment of the invention when the gases have different concentrations.

FIG. 4 is a schematic diagram illustrating variations in current density of gases to be sensed by the semiconductor sensing device according to the third embodiment of the invention when the gases have different concentrations. With reference to FIG. 4, in the third embodiment of the invention, the material of the semiconductor sensing layer 120 includes P3HT, for instance. Here, the semiconductor sensing device 300 is placed in a nitrogen-containing environment, the to-be-sensed gas is ammonia ($NH_3$), the sensing time of gas with different concentrations is 300 seconds each time, and each returning time after sensing the to-be-sensed gas with one of the concentrations is 300 seconds as well, for instance. It can be learned from FIG. 4 that the to-be-sensed gas with the relatively high concentration allows the current density of the semiconductor sensing device 300 to decrease in a relatively fast manner, and thus the semiconductor sensing device 300 is highly sensitive as to the action of sensing gas.

Figure 5A:
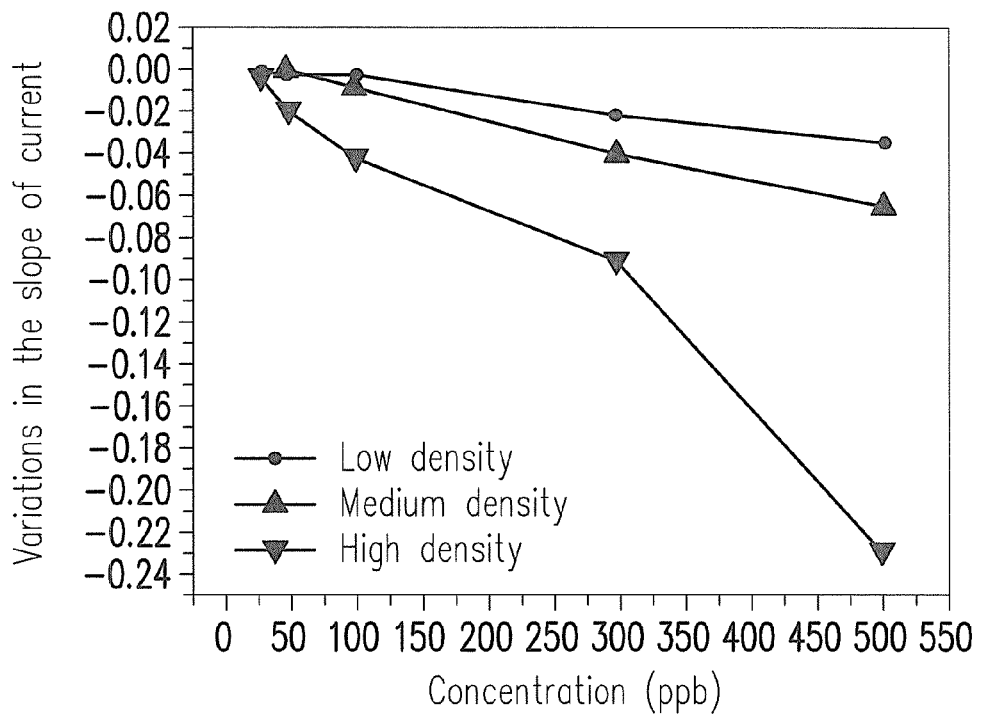
FIG. 5A is a schematic diagram illustrating variations in the slope of current while gases with different concentrations are sensed by conductive nanowires with different densities according to the third embodiment of the invention.
Figure 5B:
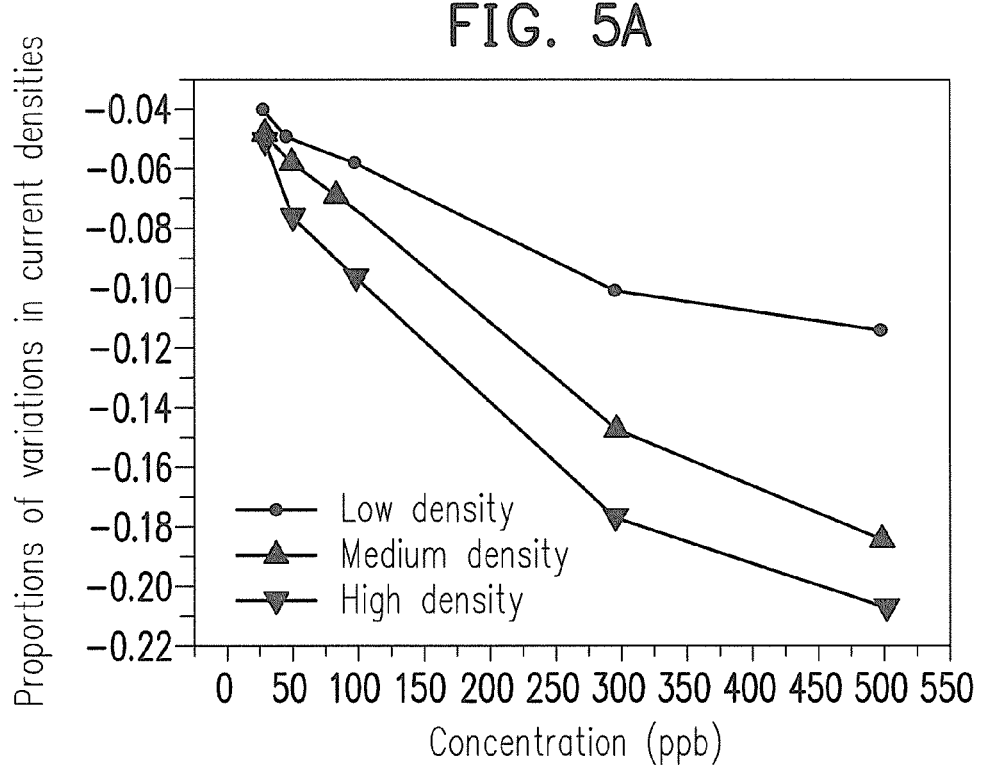
FIG. 5B is a schematic diagram illustrating proportions of variations in current densities while gases with different concentrations are sensed by conductive nanowires with different densities according to the third embodiment of the invention.

FIG. 5A is a schematic diagram illustrating variations in the slope of current while gases with different concentrations are sensed by conductive nanowires with different densities according to the third embodiment of the invention. FIG. 5B is a schematic diagram illustrating proportions of variations in current densities while gases with different concentrations are sensed by conductive nanowires with different densities according to the third embodiment of the invention. Particularly, as shown in FIG. 3E, FIG. 5A, and FIG. 5B, the conductive nanowires 112 in the nanowire conductive layer 110 are made of silver, for instance, and the conductive nanowires 112 can be dissolved in isopropyl alcohol (IPA) to prepare the solution. After dissolving different number of conductive nanowires 112, the resultant nanowire conductive layer 110 formed by drop casting may have the conductive nanowires with different densities. Particularly, FIG. 5A shows the data points right after the to-be-sensed gas (e.g., $NH_3$) is added, and FIG. 5B shows the data points five minutes after the to-be-sensed gas (e.g., $NH_3$) is added. According to the present embodiment as shown in FIG. 5A and FIG. 5B, the higher the density of the conductive nanowires 112, the greater the sensitivity of the semiconductor sensing device 300.

To sum up, the semiconductor sensing device provided in an embedment of the invention has the nanowire conductive layer with the gaps that allow the expansion of the contact area between the semiconductor sensing layer and the external air as well as the to-be-sensed gas, thus enhancing the sensing sensitivity. The conductive nanowires of the nanowire conductive layer can also be prevented from being inserted into the gaps in the semiconductor sensing layer with the microstructures. In another aspect, according to the manufacturing method of the semiconductor sensing device provided herein, the nanowire conductive layer applicable to the semiconductor sensing layer with the microstructures can be formed on the semiconductor sensing layer by drop casting, so as to form the highly sensitive semiconductor sensing device.

Although the invention has been described with reference to the above embodiments, it will be apparent to one of ordinary skill in the art that modifications to the described embodiments may be made without departing from the spirit of the invention. Accordingly, the scope of the invention will be defined by the attached claims and not by the above detailed descriptions.

What is claimed is:

1. A semiconductor sensing device comprising:
   a nanowire conductive layer comprising a plurality of connected conductive nanowires, wherein gaps are formed between the conductive nanowires;
   a semiconductor sensing layer electrically connected to the nanowire conductive layer;
   a conductive layer electrically connected to the semiconductor sensing layer, wherein the semiconductor sensing layer is located between the nanowire conductive layer and the conductive layer;
   a substrate, the conductive layer being located between the semiconductor sensing layer and the substrate; and
   a dielectric layer located between the semiconductor sensing layer and the conductive layer and between the semiconductor sensing layer and the substrate, wherein the conductive layer covers one portion of the substrate, the dielectric layer covers one portion of the conductive layer and another portion of the substrate, the semiconductor sensing layer covers the dielectric layer and another portion of the conductive layer exposed by the dielectric layer, and the nanowire conductive layer is located on the semiconductor sensing layer.

2. The semiconductor sensing device as recited in claim 1, wherein the conductive nanowires are connected in a random manner, so as to form the nanowire conductive layer.

3. The semiconductor sensing device as recited in claim 1, wherein the semiconductor sensing layer comprises a plurality of semiconductor sensing pillars extending along a direction from the conductive layer to the nanowire conductive layer.

4. The semiconductor sensing device as recited in claim 1, wherein a material of the semiconductor sensing layer comprises an organic semiconductor material.

5. The semiconductor sensing device as recited in claim 1, wherein a material of the semiconductor sensing layer comprises an inorganic semiconductor material.

6. The semiconductor sensing device as recited in claim 1, wherein a material of the semiconductor sensing layer comprises indium-gallium-zinc oxide, tin dioxide, zinc oxide, iron oxide, or a combination thereof.

* * * * *